United States Patent [19]

Beck

[11] Patent Number: 4,555,577

[45] Date of Patent: Nov. 26, 1985

[54] 2,4-DICHLORO-5-THIAZOLECARBOXALDEHYDE AND A PROCESS FOR ITS PREPARATION

[75] Inventor: Gunther Beck, Leverkusen, Fed. Rep. of Germany

[73] Assignee: Bayer Aktiengesellschaft, Leverkusen, Fed. Rep. of Germany

[21] Appl. No.: 576,183

[22] Filed: Feb. 2, 1984

[30] Foreign Application Priority Data

Feb. 4, 1983 [DE] Fed. Rep. of Germany ....... 3303704

[51] Int. Cl.$^4$ ............................................ C07D 277/20
[52] U.S. Cl. ...................................... 548/200; 548/205
[58] Field of Search ................................ 548/200, 205

[56] References Cited

U.S. PATENT DOCUMENTS 4,395,544  7/1983  Egli ...................................... 592/413

OTHER PUBLICATIONS

Sandler, Organic Functional Group Preparations vol. III, pp. 378–379, (1972).

*Primary Examiner*—Robert Gerstl

*Attorney, Agent, or Firm*—Sprung, Horn, Kramer & Woods

[57] ABSTRACT

The new 2,4-dichloro-5-thiazolecarboxaldehyde of the formula

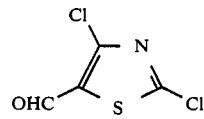

can be prepared in good yields by reacting 2,4-thiazolidinedione (III) with 1–1.5 mol of dimethylformamide and 3–10 mol of phosphorus oxychloride at the reflux temperature of the reaction mixture (about 115° C.) until evolution of HCl gas has ended, and then working up hydrolytically.

The aldehyde (II) can readily be converted, via the new oxime (IV), into the corresponding nitrile, 2,4-dichloro-5-cyanothiazole (V), which is a known intermediate for the preparation of herbicidal active compounds of the thiazolyloxyacetamide type.

5 Claims, No Drawings

2,4-DICHLORO-5-THIAZOLECARBOXALDEHYDE AND A PROCESS FOR ITS PREPARATION

The present application relates to the new 2,4-dichloro-5-thiazolecarboxaldehyde and a process for its preparation.

The reaction between 2,4-thiazolidinedione (III), dimethylformamide and phosphorus oxychloride is described in Khim. Geterotsikl. Soedin 1975, page 85 (English translation: Chem. Het. Comp. 1975, page 73). In this reaction, the three substances mentioned are, in an optimum molar ratio of 1:1.5:3, heated at 80° C. for 16 hours and at 115° to 130° C. for a short time and then hydrolyzed, whereupon 4-chloro-2,3-dihydro-2-oxo-5-thiazolecarboxaldehyde of the formula (I)

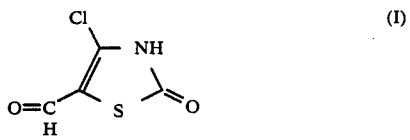

is obtained in 40 to 60% yield.

It has now been found, surprisingly, that the new 2,4-dichloro-5-thiazolecarboxaldehyde of the formula (II)

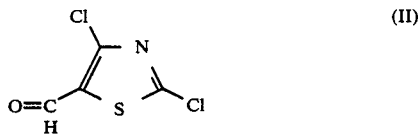

is obtained in good yields by reacting 2,4-thiazolidinedione of the formula (III)

with 1 to 1.5 mol of dimethylformamide and 3 to 10 mol of phosphorus oxychloride at the reflux temperature of the reaction mixture (about 115° C.) until evolution of hydrogen chloride gas has ended, and then working up hydrolytically.

The course of the reaction can be represented by the diagram below

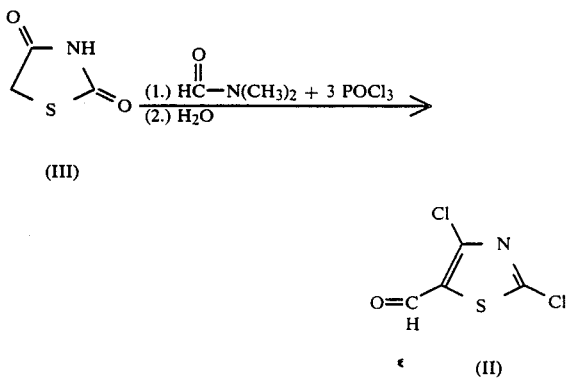

The 2,4-thiazolidinedione (III) to be used as the starting material is known and can be prepared, for example, by reaction of chloroacetic acid with thiourea in an aqueous medium (compare, for example, Journal für Praktische Chemie [2] 9, page 9 (1874)).

In carrying out the process according to the invention, 1 to 1.5 mol, preferably 1 to 1.1 mol of dimethylformamide and 3 to 10 mol, preferably 4.5 to 6 mol, (50 to 100% excess) of phosphorus oxychloride are generally employed for 1 mol of 2,4-thiazolidinedione (III).

Specifically, the process is carried out in such a manner that dimethylformamide is added dropwise to phosphorus oxychloride, which has been initially introduced, while cooling in the temperature range from about 0° C. to 20° C. It is possible to add the 2,4-thiazolidinedione either before or after addition of the dimethylformamide. The reaction mixture is then heated at reflux temperatures (about 110°–120° C.) until the evolution of hydrogen chloride gas has ended. Depending on the ratios of amounts of the participants in the reaction, on the size of the batch etc., the reaction lasts between about 1 and 10 hours. After mixing the reactants, it can be advantageous for the process initially to stir them for a period (for example 1 hour) at room temperature or below before heating up. Furthermore, it can be advantageous not to carry out the heating to reflux temperatures uninterruptedly but, in periods of extensive evolution of hydrogen chloride gas, for example in the range about 80° C., to interrupt it for a time (for example about one to two hours) and not heat further until the reaction has subsided.

Working up is carried out in a customary manner by carefully discharging onto ice or into cold water with external cooling, and extracting the 2,4-dichloro-5-thiazolecarboxaldehyde with an organic solvent which is immiscible with water (for example methylene chloride or diethyl ether). Purification of the crude 2,4-dichloro-5-thiazolecarboxaldehyde which remains after evaporation of the organic solvent can be by all conventional methods, such as distillation, crystallization (for example from petroleum ether) or by chromatographic means. The yields of isolated product which is pure by gas chromatography are 50–60% of theory.

2,4-Dichloro-5-thiazolecarboxaldehyde (II) can be used as an intermediate for the synthesis of known herbicidal active compounds. For this purpose, the aldehyde is initially converted in a customary manner, for example by reaction at 0°–50° C. with 1–1.1 mol hydroxylamine, advantageously in the form of its hydrochloride, per mol of the aldehyde, preferably in water as a solvent, into its oxime of the formula (IV).

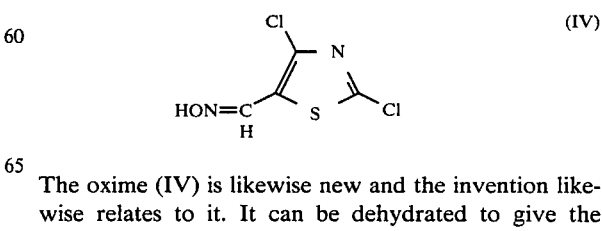

The oxime (IV) is likewise new and the invention likewise relates to it. It can be dehydrated to give the known nitrile of the formula (V)

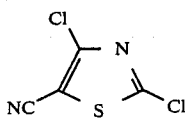

likewise by conventional methods, for example by heating with 1-20 mols, preferably 1-10 mols of acetic anhydride per mol of the oxime at 100°-150° C. and a pressure of 1-5 bar, preferably at reflux temperature under normal pressure. This nitrile can be reacted, as described in German Offenlegungsschrift No. 3,038,608, with hydroxyacetamides to give herbicidal active compounds of the thiazolyloxyacetamide type, for example with hydroxyacetic N-methylanilide to give O-(2,4-dichloro-5-cyano-2-thiazolyl)oxyacetic N-methylanilide of the formula (VI).

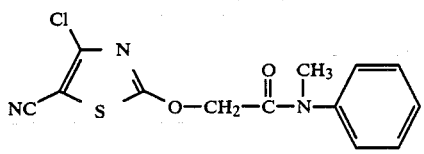

(VI)

The new process for the preparation of the nitrile (V)—by the route (III)→(II)→(IV)→(V)—is industrially superior to the older methods of preparation (compare German Offenlegungsschrift No. 3,038,806), so that the herbicidal active compounds of the type (VI) have become accessible by the invention in a considerably improved manner.

PREPARATION EXAMPLES (A) Preparation of 2,4-dichloro-5-thiazolecarboxaldehyde (II)

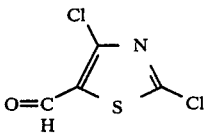

(II)

EXAMPLE 1

32.1 g (0.44 mol) of dimethylformamide are added dropwise, in 15 minutes, to a suspension of 46.8 g (0.4 mol) of 2,4-thiazolidinedione (III) in 368 g (2.4 mol) of phosphorus oxychloride (POCl₃) with stirring at 10° to 20° C. After addition is complete, the mixture is allowed to stand at room temperature for 1 hour. It is then heated to 80° to 90° C. and stirred at 80° to 90° C. for a further hour. It is subsequently heated to reflux temperature (about 115° C.) and further stirred at this temperature until the evolution of gas has ended (about 4 hours). After cooling, the reaction mixture is slowly stirred into 2 kg of ice. The mixture is extracted three times with 500 ml of methylene chloride each time. The combined organic phases are washed with aqueous sodium bicarbonate solution, dried over sodium sulphate and concentrated by distilling out the solvent in vacuo. The residual brown oil, which partially crystallizes after some time, is initially prepurified by distilling out all the components which can be distilled up to a heating bath temperature of about 180° C. under water pump vacuum. The colourless distillate, which almost completely crystallizes at room temperature, is dried on a clay tile to remove small amounts of liquid components. 42.8 g (=58.8% of theory) of 2,4-dichloro-5-thiazolecarboxaldehyde (II), which is pure by gas chromatography, are thus obtained. Melting point after recrystallization from petroleum ether: 48°-49° C.

EXAMPLE 2

160 g (2.19 mol) of dimethylformamide are added dropwise, in 15 minutes, to a suspension of 250 g (2.14 mol) of 2,4-thiazolidinedione (III) in 1477 g (9.62 mol) of phosphorus oxychloride, with stirring at 10° to 20° C. After addition is complete, the mixture is heated to 80° to 85° C. and is stirred at 80° to 85° C. for one hour. It is subsequently heated to reflux temperature (about 115° C.) and further stirred at this temperature until evolution of gas has ended (about 8 hours). After cooling, the reaction mixture is slowly stirred into 5 liters of water, a temperature range from 10° to 20° C. being maintained by external cooling. The mixture is subsequently extracted three times with a total of about 5 liters of methylene chloride. The combined organic phases are worked up in analogy to Example 1. Yield of 2,4-dichloro-5-thiazolecarboxaldehyde (II) which is pure by gas chromatography: 216 g (=55.4% of theory).

EXAMPLE 3

The procedure is initially analogous to that in Example 2. After addition of dimethylformamide is complete, the mixture is directly heated to reflux temperature and further stirred at this temperature until evolution of gas has ended (about 8 hours). After cooling, excess phosphorus oxychloride is distilled out under water pump vacuum. 2 liters of methylene chloride are added to the remaining brown oil. 2 liters of water are now added dropwise, with vigorous stirring (stainless steel stirrer), the temperature of the reaction mixture being maintained between 10° and 20° C. by external cooling. After separating off the organic phase, the aqueous phase is extracted three more times with 1 liter of methylene chloride each time. The combined organic phases are worked up in analogy to Example 1. Yield of 2,4-dichloro-5-thiazolecarboxaldehyde (II) which is pure by gas chromatography: 211 g (=54.2% of theory).

(B) Preparation of 2,4,-dichloro-5-thiazolecarbonitrile (V)

1st step: Preparation of 2,4-dichloro-5-thiazolecarboxaldehyde oxime (IV)

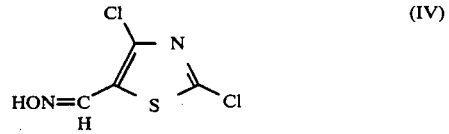

(IV)

First 153 g (2.2 mol) of hydroxylamine hydrochloride in portions, then a solution of 364 g (2 mol) of 2,4-dichloro-5-thiazolecarboxaldehyde (II) in 1 liter of ethanol are added to a solution of 185 g (2.2 mol) of sodium bicarbonate in 5 liters of water at room temperature, with stirring. A voluminous, colourless precipitate separates out after 1 to 2 minutes. After stirring for 1 hour, the solid is filtered off with suction, washed with water and dried. 390 g (=99% of theory) of 2,4-dichloro-5-thiazolecarboxaldehyde oxime (IV) of melting point about 160° C. are obtained. It can be dehydrated to give the nitrile without further purification.

2nd step: Preparation of 2,4-dichloro-5-thiazolecarbonitrile (V)

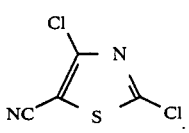

(V)

400 g (2.03 mol) of crude 2,4,-dichloro-5-thiazolecarboxaldehyde oxime (IV) are stirred with 2 liters of acetic anhydride at reflux temperature (137° C.) for 4 hours. Fractionation using a silvered distillation column 1 m long provided 271 g (=75.7% of theory) of 2,4-dichloro-5-thiazolecarbonitrile (V) at 112° C./20 m bar, this product being identical by mass and IR spectroscopy with that described in German Offenlegungsschrift No. 3,038,608 (which can also be named 2,4-dichloro-5-cyanothiazole). The compound solidifies at room temperature to give colourless crystals which can be recrystallized from petroleum ether. Melting point: 34°–35° C.

What is claimed is:

1. 2,4-dichloro-5-thiazolecarboxaldehyde of the formula

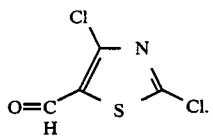

2. A process for preparing a 2,4-dichlor-5-thiazolecarboxaldehyde of the formula

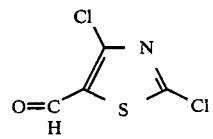

which comprises contacting, 2,4-thiazolidinedione of the formula

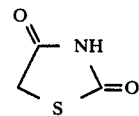

with 1–1.5 mols of dimethylformamide and 3–10 mol of phosphorus oxychloride at the reflux temperature of the reaction mixture until evolution of hydrogen chloride gas has ceased and thereafter working up the reaction mixture hydrolytically.

3. A process according to claim 2, wherein 1–1.1 mols of dimethylformamide are employed per mol of 2,4-thiazolidinedione.

4. A process according to claim 2, wherein 4.5–6 mols of phosphorus oxychloride are employed per mol of 2,4-thiazolidinedione.

5. 2,4-dichloro-5-thiazolecarboxaldehyde oxime of the formula

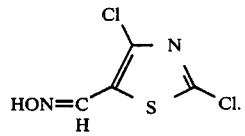

* * * * *